United States Patent [19]

Linhart et al.

[11] 4,348,335

[45] Sep. 7, 1982

[54] PROCESS FOR THE PARTIAL REDUCTION OF POLYNITRATED DIARYL COMPOUNDS

[75] Inventors: Karl Linhart; Dieter Pawellek, both of Leverkusen; Harald Gleinig, Odenthal, all of Fed. Rep. of Germany

[73] Assignee: Bayer Aktiengesellschaft, Leverkusen, Fed. Rep. of Germany

[21] Appl. No.: 139,952

[22] Filed: Apr. 14, 1980

[30] Foreign Application Priority Data

Apr. 26, 1979 [DE] Fed. Rep. of Germany ....... 2916815

[51] Int. Cl.$^3$ ............................................. C07C 143/29
[52] U.S. Cl. .................... 260/508; 260/509; 260/510; 564/416; 564/417; 564/307; 564/315
[58] Field of Search ....................... 260/508, 509, 510; 564/416, 417, 307, 315

[56] References Cited

U.S. PATENT DOCUMENTS

| | | | |
|---|---|---|---|
| 2,149,474 | 3/1939 | Straub et al. ........................ | 260/509 |
| 2,649,479 | 8/1953 | Zickendraht ........................ | 260/508 |
| 2,669,584 | 2/1954 | Lowe ................................... | 564/416 |
| 4,115,652 | 9/1978 | Linhart et al. ....................... | 568/706 |

OTHER PUBLICATIONS

Sarbort et al., Chem. Abstract, 86, 155,368a (1977) (Abstract of Czechoslovakian Patent 165,231).
Grundlegende Operation en der Farbenchemie, pp. 109–110 (1952).

*Primary Examiner*—Nicky Chan
*Attorney, Agent, or Firm*—Sprung, Horn, Kramer & Woods

[57] ABSTRACT

Polynitrated diaryl compounds of the formula given in the description are reduced with 1-2 mols of sulphides, or compounds which donate sulphide ions, per mol of nitro group in the presence of 0.5-10 mols of ammonia per mol of starting compound at 30°–110° C. to give nitroamino-diaryl compounds, for example 4,4'-dinitro-dibenzyl-2,2'-disulphonic acid is reduced to 4-nitro-4'-amino-stilbene-2,2'-disulphonic acid.

7 Claims, No Drawings

PROCESS FOR THE PARTIAL REDUCTION OF POLYNITRATED DIARYL COMPOUNDS

The present invention relates to a process for the partial reduction of polynitrated diaryl compounds to give nitroaminodiaryl compounds, in particular of compounds of the general formula

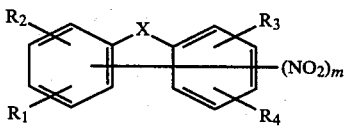

wherein
X=O, Sy, with y=1 or 2, SO, SO₂, NH, (CH₂)$_p$, with p=0, 1 or 2,

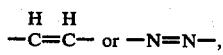

R₁, R₂, R₃ and R₄ independently of one another=hydrogen, C₁-C₄-alkyl, halogen or sulphonic acid groups and
m=a number from 2 to 10,
to give nitroaminodiaryl compounds of the general formula

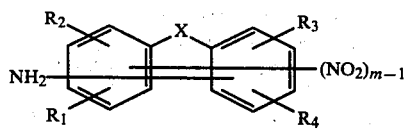

in aqueous or organic solution or suspension using sulphides or substances which donate sulphide ions, characterised in that, per nitro group to be reduced, 1–2 mols, preferably equivalent amounts, that is to say 1.5 mols, of sulphide are used and the reaction is carried out at elevated temperature in the presence of 0.5–10 mols of ammonia per mol of starting compound of nitro group to be reduced.

Specific examples of polynitrated diaryl compounds which may be mentioned are: 4,4'-dinitro-biphenyl, 4,4'-dinitro-diphenyl ether, 4,4'-dinitro-diphenyl thioether, 2,2'-dinitro-diphenyl disulphide, 4,4'-dinitro-diphenyl sulphone, 4,4'-dinitro-3,3'-dimethoxy-biphenyl, 4,4'-dinitro-diphenylmethane, 4,4'-dinitro-dibenzyl ether, 4,4'-dinitro-diphenylamine, 2,2'-dinitro-4,4'-bis-dimethylamine-diphenylmethane, 2,4-dinitro-2'-hydroxydiphenylamine, 2,4-dinitro-2'-hydroxy-5'-chloro-diphenylamine, 4,4'-dinitro-dibenzyl-2,2'-disulphonic acid, 4,4'-dinitro-stilbene-2,2'-disulphonic acid and 1-hydroxy-8-amino-naphthalene-3,6-(disulphonic acid) 2,7-bis-(4-nitro-diazobenzene).

The statements made in BIOS Final Report 1153, 197 (1948) regarding the partial reduction of 4,4'-dinitrostilbene-2,2'-disulphonic acid cannot be confirmed when the reduction is repeated. A molar ratio of 0.68 mol of hydrogen sulphide per mol of nitro group cannot be sufficient in the desired sense, for stoichiometric reasons alone. In particular, neither a high conversion nor a high selectivity is achieved at the temperatures of 38° to 43° C. indicated in this report. Investigation of the reaction mixture obtained clearly shows that the instructions indicated in the BIOS report do not lead to the desired success. The 4-nitro-4'-amino-stilbene-2,2'-disulphonic acid postulated is formed in a yield of only 43%. About 53.5% of non-reduced starting material remains. The rest has been reduced to 4,4'-diaminostilbene-2,2'-disulphonic acid.

The most diverse sulphide compounds are suitable for the reduction, for example sodium bisulphide, and also alkali metal sulphides and alkaline earth metal sulphides as well as ammonium sulphides.

The temperature can be chosen within wide limits. The reduction is advantageously carried out in the range from 30° to 110° C., in particular at 75°–85° C. At the optimum temperatures, the reductions proceed so rapidly that they can also be carried out continuously.

The possibility of carrying out the process industrially may be illustrated by the following example of the partial reduction of 4,4'-dinitro-stilbene-2,2'-disulphonic acid or alkali metal salts thereof to give 4-nitro-4'-amino-stilbene-2,2'-disulphonic acid or alkali metal salts thereof:

An aqueous solution of the disodium salt of 4,4'-dinitro-stilbene-2,2'-disulphonic acid is treated with an equivalent amount, relative to the nitro group to be reduced, of sodium bisulphide solution at 75°–85° C., ammonia being added. The course of the reaction can be followed by known analytical methods. When the partial reduction has ended, the 4-nitro-4'-amino-stilbene-2,2'-disulphonic acid formed is isolated as the disodium salt or as an inner salt. The amount of 4,4'-diamino-stilbene-2,2'-disulphonic acid contained as an impurity is less than 1% and the residual content of 4,4'-dinitro-stilbene-2,2'-disulphonic acid is less than 0.1%. 4-Nitro-4'-aminostilbene-2,2'-disulphonic acid is a known intermediate product for dyestuffs.

EXAMPLE 1

(Control experiment in accordance with the method of the BIOS Final Report 1153, 197 (1948) I. G. Farben on the partial reduction of 4,4'-dinitro-stilbene-2,2'-disulphonic acid).

996 g of a 43.2% strength by weight product paste containing 430 g (1.0 mol) of 4,4'-dinitro-stilbene-2,2'-disulphonic acid are diluted with water to give a 22.8% strength by weight suspension. On warming to 55° C., according to the instructions, no solution is obtained. Even under reflux, a suspension is present. 23 g (0.68 mol) of hydrogen sulphide, in the form of 38.1 g of sodium bisulphide, in 163.4 g=148.5 ml of a 23.3% strength by weight sodium bisulphide solution (D: 1.1) are allowed to run into the stirred suspension, whereupon the temperature rises from 38° C. to 43° C. and, after 45 minutes, falls again to 38° C. Thereafter, 200 ml of concentrated hydrochloric acid are added and air is bubbled through the strongly acid solution for 2 hours in order to remove the sulphur dioxide liberated. The product is isolated.

According to the result of an analysis, about 53.5% of unreacted starting material and about 3.5% of 4,4'-diamino-stilbene-2,2'-disulphonic acid are present, in addition to 43% of 4-nitro-4'-amino-stilbene-2,2'-disulphonic acid. On adding a further 148.5 ml of a 23.3% strength by weight sodium bisulphide solution, the batch, now present in a clear form, is composed of 16.7% of 4,4'-dinitro-, 56.8% of 4-nitro-4'-aminostilbene- and 26.5% of 4,4'-diamino-stilbene-2,2'-disulphonic acid.

EXAMPLE 2

906.4 g of a 52.3% strength by weight product paste, containing 474 g (1 mol) of disodium 4,4'-dinitrostilbene-2,2'-disulphonate, are heated to 75°–85° C., 1,000 ml of water and 336 ml=306 g of 25% strength by weight ammonium hydroxide solution (D: 0.9), containing 76.5 g (4.5 mols) of ammonia, being added, whereupon a dark red, clear solution which is 21.3% strength by weight, relative to dinitrostilbenedisulphonic acid, results. A mixture of 244 ml of a 34.4% strength by volume sodium bisulphide solution, containing 84 g (1.5 mols) of sodium bisulphide, and 37 ml=34 g of 25% strength by weight ammonium hydroxide solution, containing 8.5 g (0.5 mol) of ammonia, is metered into the solution in the course of 1 hour. Analysis of the reaction mixture clearly shows a selective and virtually quantitative removal of one nitro group in the molecule by reduction. The mixture is acidified down to a pH of 3.9 with concentrated hydrochloric acid. After cooling the mixture to room temperature, the red paste is filtered off. According to analysis, the 1,310 g of paste are 30.5% strength, that is to say 399.6 g of product are present, which corresponds to a yield of 99.8% of theory. Based on 100 g of 100% pure goods, the 4-nitro-4'-amino-stilbene-2,2'-disulphonic acid contains only 1 g of 4,4'-diamino-stilbene-2,2'-disulphonic acid and less than 0.1% of 4,4'-dinitro-stilbene-2,2'-disulphonic acid.

EXAMPLE 3

572.9 g of a 75.4% strength by weight starting material, containing 432 g (1 mol) of 4,4'-dinitro-dibenzyl-2,2'-disulphonic acid are dissolved in 850 ml of water, after adding 151 ml=136 g of a 25% strength by weight ammonium hydroxide solution, containing 34 g (2 mols) of ammonia, and whilst warming. 244 ml of a 34.4% strength by volume sodium bisulphide solution, containing 84 g (1.5 mols) of NaHS, are metered in at a temperature of 80° C. in the course of 2 hours. The yield of 4-nitro-4'-amino-dibenzyl-2,2'-disulphonic acid is 265 g=98% of theory.

EXAMPLE 4

280.6 g of a 98% strength by weight starting material, containing 275 g (1 mol) of 2,4-dinitro-2'-hydroxy-diphenylamine are dissolved by adding 800 ml of water and 75.6 ml=68 g of a 25% strength by weight ammonium hydroxide solution, containing 17 g (1 mol) of ammonia, and by warming the mixture to 80°–90° C. 244 ml of a 34.4% strength by volume sodium bisulphide solution, containing 84 g (1.5 mols) of NaHS, are metered into the solution in the course of 2 hours. The yield of 4-nitro-2-amino-2'-hydroxy-diphenylamine is 240 g=98% of theory.

EXAMPLE 5

311 g of a 99.1% strength by weight starting material, containing 308 g (1 mol) of 4,4'-dinitrodiphenyl sulphone, are suspended in 800 ml of water and, after adding 75.6 ml=68 g of a 25% strength by weight ammonium hydroxide solution, containing 17 g (1 mol) of ammonia, the mixture is charged with 244 ml of a 34.4% strength by volume sodium bisulphide solution, containing 84 g (1.5 mols) of NaHS, at 80°–90° C. The yield of 4-nitro-4'-amino-diphenyl sulphone is 272 g=98% of theory.

EXAMPLE 6

280 g of a 99.4% strength by weight starting material, containing 276 g (1 mol) of 4,4'-dinitrodiphenyl sulphide, are suspended in 800 ml of water and, after adding 75.6 ml=68 g of a 25% strength by weight ammonium hydroxide solution, containing 17 g (1 mol) of ammonia, the mixture is charged with 244 ml of a 34.4% strength by volume sodium bisulphide solution, containing 84 g (1.5 mols of NaHS) at 80°–90° C. The yield of 4-nitro-4'-amino-diphenyl sulphide is 212 g=98% of theory.

I claim:
1. Process for the preparation of 4-nitro-4-aminostilbene-2,2'-disulphonic acid or alkali metal salts thereof by reducing 4,4'-dinitro-stilbene-2,2'-disulphonic acid or alkali metal salts thereof with sulphides, or substances which donate sulphide ions, at elevated temperature, characterised in that the reduction is carried out with equivalent amounts of sulphide per mol of nitro group to be reduced and in the presence of 0.5–10 mols of ammonia per mol of starting compound.
2. Process according to claim 1, characterised in that the reduction is carried out at 30°–110° C.
3. Process according to claim 1 or 3 characterised in that the reduction is carried out with bisulphides of the alkali metals, alkaline earth metals and of ammonia.
4. Process according to claim 1, characterised in that disodium 4,4'-dinitro-stilbene-2,2'-disulphonate is converted into 4-nitro-4'-aminostilbene-2,2'-disulphonic acid or a salt thereof.
5. Process according to claim 2 characterised in that the reduction is carried out at 70°–90° C.
6. Process according to claim 2 characterised in that the reduction is carried out at 75°–85° C.
7. Process according to claim 3 wherein the bisulphide is sodium bisulphide.

* * * * *